United States Patent [19]

Allen et al.

[11] 4,134,799
[45] Jan. 16, 1979

[54] METHOD FOR SELECTING A DEMULSIFIER FOR BREAKING A WATER-IN-OIL EMULSION

[75] Inventors: Wallace B. Allen, Dallas; John W. Harrell, Duncanville; William W. Webster, Arlington, all of Tex.

[73] Assignee: Mobil Oil Corporation, New York, N.Y.

[21] Appl. No.: 816,562

[22] Filed: Jul. 18, 1977

[51] Int. Cl.² ............................................ G01N 27/46
[52] U.S. Cl. .............................. 204/1 T; 204/195 R; 324/30 R
[58] Field of Search ........................ 204/1 T, 195 R; 324/30 R

[56] References Cited

U.S. PATENT DOCUMENTS

| B 275,426 | 1/1975 | Costas | 204/1 T |
|---|---|---|---|
| 2,678,911 | 5/1954 | Chittum | 204/185 |
| 2,859,404 | 11/1958 | Crittendon | 324/30 |
| 4,023,096 | 5/1977 | Schmidt | 204/1 T |
| 4,029,554 | 6/1977 | Ellison | 204/1 T |

Primary Examiner—T. Tung
Attorney, Agent, or Firm—C. A. Huggett; George W. Hager, Jr.

[57] ABSTRACT

A method for selecting a demulsifier for breaking a water-in-oil emulsion employs at least two electrodes to be immersed in a plurality of emulsion samples, each having a different demulsifier added. The current flow between the electrodes is recorded for each sample. The demulsifier producing the most rapid rate of change of current flow is identified as the most effective demulsifier in breaking the water-in-oil emulsion.

5 Claims, 2 Drawing Figures

METHOD FOR SELECTING A DEMULSIFIER FOR BREAKING A WATER-IN-OIL EMULSION

BACKGROUND OF THE INVENTION

This invention relates to the separation of a water-in-oil emulsion into separate water and oil phases. More particularly, the present invention relates to the selection of a demulsifier for use in the separation of such emulsions into water and oil phases.

In oil fields, water usually is produced with crude oil. The complexity of separating mixtures of water and oil depends upon the physical form of the water. Where the mixture has only "free" water, the water will separate readily from the oil because of the differences in gravities of the water and oil. This type of separation presents no problem other than providing a vessel in which water-oil phase separation can occur. However, the water can be dispersed throughout the oil in very minute particles, usually with diameters less than 25 microns. This mixture may be termed a stable emulsion and is very difficult to separate into water and oil phases.

The breaking of stable water-in-oil emulsions may be achieved by physical and chemical treatments, application of heat, and electrical methods, or by a combination of these treatments. In many instances chemical demulsifiers are added to the emulsion to counteract the effects of emulsifiers which provide the stability of the dispersed water particles in the oil phase. There are a magnitude of complex chemical compositions which serve as demulsifiers. Surface-active materials have been used successfully as demulsifiers. The demulsifiers usually have a variety of polar components with a preferred solubility ranging from predominantly oil-soluble to predominantly water-soluble.

The selection of a demulsifier for breaking a particular emulsion has, in the past, been based primarily on trial-and-error procedures. There is, therefore, a real need for a more effective method for determining the performance of demulsifiers in breaking and controlling water-in-oil emulsions.

SUMMARY OF THE INVENTION

In accordance with the present invention, a demulsifier is selected for breaking a water-in-oil emulsion into its constituent phases. In a first step, at least two electrodes are immersed in a sample of the emulsion. An AC voltage is applied to these electrodes and the rate of change of current flow between the electrodes is recorded as the emulsion breaks down under such voltage. In a second step, a demulsifier is selected and added to another sample of the emulsion. The two electrodes are immersed into the emulsion sample, and the AC voltage applied. The rate of change of current flow between the electrodes is again recorded as the emulsion breaks down. The foregoing steps are repeated for a plurality of selected demulsifiers. The demulsifier which provides for the most rapid rate of change of current flow between the electrodes can be identified as the most effective in breaking the particular water-in-oil emulsion.

In a further aspect of the invention, the foregoing steps may be repeated with differing amounts of each demulsifier to identify the most effective concentration of the demulsifier in breaking the water-in-oil emulsion.

In a still further aspect of the invention, a third electrode may be immersed in the emulsion sample. Each positive half cycle of the AC voltage is applied across a first pair of the electrodes. Each negative half cycle of the AC voltage is applied across a second pair of the electrodes. The rate of change of current flow through the common electrode of the two pairs of electrodes is recorded in order to identify the most effective demulsifier in breaking the water-in-oil emulsion.

DESCRIPTION OF THE PREFERRED EMBODIMENT

Figure 1:
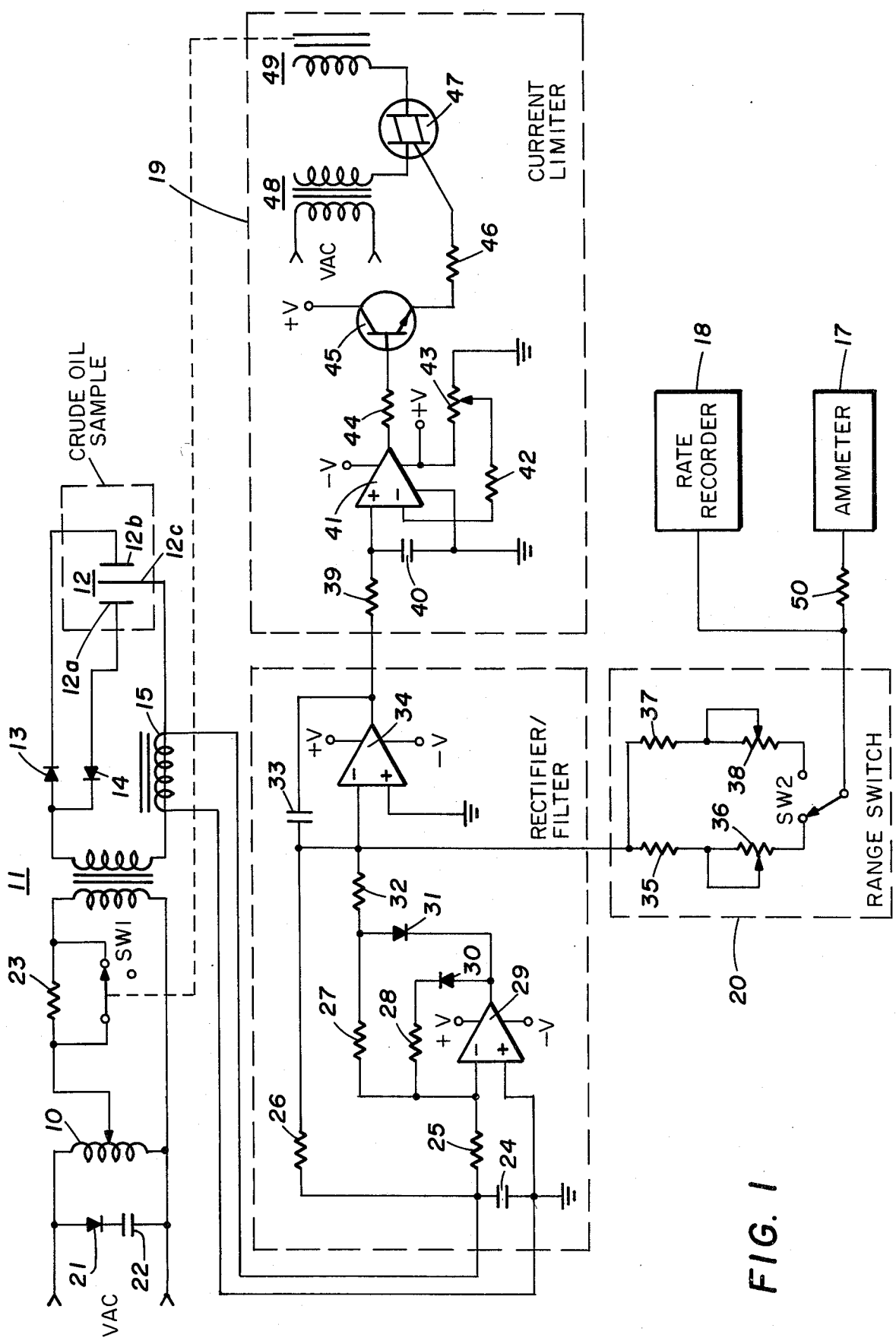
FIG. 1 is an electrical schematic of a system which may be used for the practice of the steps of the present method in identifying demulsifiers for the separation of water-in-oil emulsions into water and oil phases.

Referring to FIG. 1, there is shown a detailed circuit diagram of a system which may be utilized in carrying out the steps of the method of the present invention of selecting demulsifiers for the separation of water from crude oil samples. An AC power source (not shown) is applied to the adjustable autotransformer 10 which controls the primary voltage of high-voltage transformer 11. A first lead from the secondary of the high-voltage transformer 11 is connected through rectifiers 13 and 14 to electrodes 12a and 12b, respectively, of an electrode cell 12. The other lead from the high-voltage transformer 11 is connected through a current transformer 15 to a third electrode 12c of the electrode cell. The electrode cell is placed in a sample of the crude oil which is to be tested for the purpose of identifying a suitable demulsifier for breaking the oil out of the crude oil prior to the refining process. When a high voltage, such as 12 kilovolts, for example, is applied to the electrodes of the cell 12, the emulsion resistivity is low, and a pulsating DC voltage of opposite polarity is present at electrodes 12a and 12b in respect to electrode 12c. The current flowing in electrode 12c, resulting from the opposite polarity potentials at electrodes 12a and 12b due to the reversed connections of the rectifiers 13 and 14 to the electrodes 12a and 12c, respectively, is an AC current. This AC current is detected by the current transformer 15. As the water coalesces and falls between the electrodes under the presence of high voltage, the oil becomes drier and the emulsion resistivity increases, resulting in electrodes 12a and 12b charging to a DC potential of opposite polarity with respect to electrode 12c. As this DC potential increases, the smaller water droplets coalesce and fall from between the electrodes, resulting in higher emulsion resistivity. As this process continues, emulsion resistivity will become sufficiently large such that electrode 12a was charged to the positive peak value of the secondary voltage of the transformer 11 and electrode 12b was charged to the negative peak value in respect to electrode 12c. When this occurs, the oil is dry and the AC current in electrode 12c and transformer 15 is zero. Therefore, by plotting this current versus time under the application of different demulsifiers to the crude oil sample under test, a selection of the most effect demulsifier for breaking down the crude oil can be carried out in accordance with the present invention.

The current transformer 15 develops a voltage proportional to the AC current flowing in electrode 12c and applies this voltage to the input of a rectifier filter circuit 16. The output of the rectifier filter 16 drives ammeter 17, recorder 18, and a current limiter 19. The output of the rectifier filter 16 is adjusted for either 50-milliamp or 100-milliamp operation by means of the range switch 20. The current limiter 19 controls the primary voltage of the high-voltage transformer 11 by limiting its operating current to the value selected by the range switch 20. This voltage control to the transformer 11 is by way of the output relay 49 of the current limiter 19 which either inserts or removes the resistor 23 from series connection with the primary of transformer 11.

In accordance with one embodiment of the present invention, TABLE I sets forth types and values of circuit components as illustrated in the drawing of FIG. 1.

The foregoing-described circuits of FIG. 1 have been developed for use in the method of the present invention to select a proper demulsifier for the most rapid and efficient breakdown of a crude oil emulsion. The steps carried out in this method will now be described in conjunction with the curves illustrated in FIG. 2. Initially, a sample of the crude oil is subjected to high voltage, preferably in excess of about 5 to 6 kilovolts, by way of the electrode cell 12 to determine its breakdown rate without the presence of a demulsifier. This rate is illustrated by the curve lableled X in FIG. 2, the curve being that which is recorded by way of the recorder 18 in response to the rate of change of current flow through the current transformer 15 in series with the electrode 12c. Next, a selected chemical a is utilized as a demulsifier and injected into the crude oil sample. High voltage is again applied to the sample and the breakdown rate again recorded by recorder 18. Such a curve may be that as illustrated at A in FIG. 2. Another chemical b is then selected and applied to another sample of the crude oil. Again, upon application of high voltage to the sample, a breakdown rate is recorded; and, if the chemical b is a more effective demulsifier for the particular crude oil sample, the breakdown rate will be more rapid as illustrated by the curve B in FIG. 2. These steps of the method of the present invention may be continued until a chemical, c, for example, is found which most rapidly breaks down the crude oil sample to a dry state as illustrated by the curve C in FIG. 2.

Figure 2:
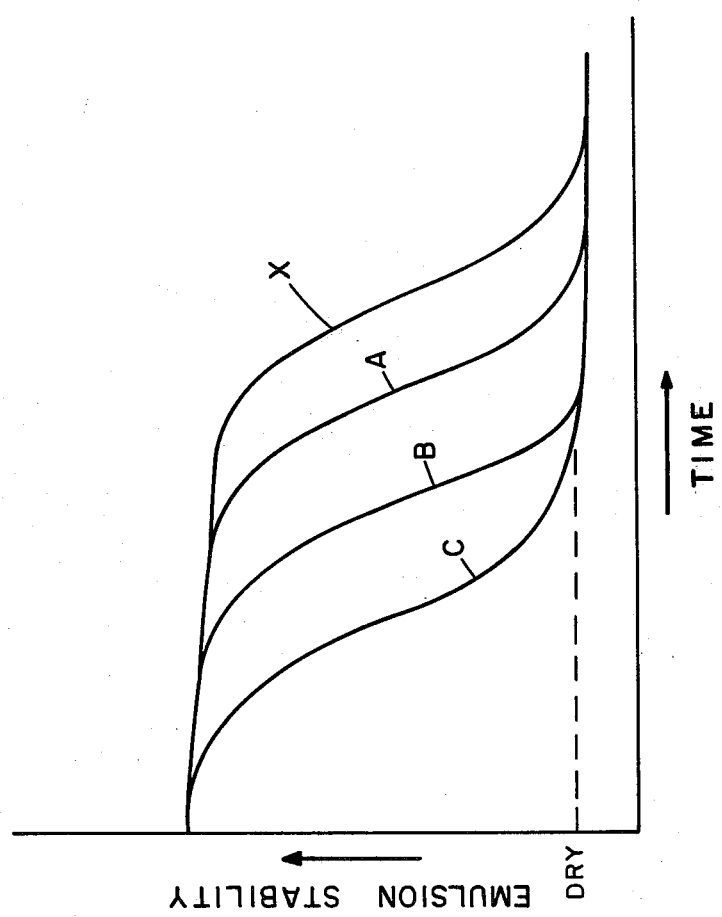
FIG. 2 is a set of curves representing the breakdown rate of a water-in-oil emulsion in the presence of various demulsifiers.

In addition to the steps of selecting various chemicals for demulsifiers and measuring the breakdown rates of the oil sample in the presence of these chemicals, the concentrations of the chemicals may also be varied and curves similar to those illustrated in FIG. 2 recorded for each different concentration for the chemicals to identify the specific concentration of each chemical that allows for the most effective breakdown of the oil sample. Accordingly, under the steps of the method of the present invention, both the particular demulsifier and the concentration of that demulsifier which most rapidly breaks down the oil sample may be selected and this demulsifier then utilized in the refining process to drive the water from the oil sample so as to present a dry oil to the refining process.

The particular chemicals selected to be tested as demulsifiers may be any one selected from those which can be employed to assist in the breaking and separating of water and oil phases from emulsions. The demulsifier is readily employed when it is in the form of a hydrocarbon solvent which can counteract the emulsifier stabilizing the dispersed water in the oil phase of the emulsion.

Emulsion-breaking chemicals are an essential part of treating on most leases that produce emulsified crude. Many chemicals have been used in the past, including such compounds as ferrous sulfate, soda ash, and various soaps. In the 1940s, the advent of oxyalkylation revolutionized the chemical-treating industry and cut the costs of chemical treating by orders of magnitude. Oxyalkylation utilizes the reaction of ethylene oxide or propylene oxide (or both) with compounds that contain reactive functional groups, usually hydroxyl or amine groups. Thus, many cheap, naturally occurring materials can be oxyalkylated to produce demulsifying chemicals. The addition of ethylene oxide increases the water solubility of a compound, while the addition of propylene oxide increases its oil solubility. Compounds which are used as starting materials or as surface-active agents themselves for chemical demulsifiers are: (1) phenolic resins, (2) glycols, (3) glycol esters, (4) phenolic resin esters, (5) polybasic acids, (6) amine polymers, and (7) sulfonates.

TABLE I

| Reference Designation | Description |
| --- | --- |
| Transformer 10 | Model 126U (Superior Electric) |
| Transformer 11 | Model 721-521 (Neon) (Jefferson Electric) |
| Transformer 15 | Model 10 (Simpson) |
| Transformer 48 | Model F-14X (Triad) |
| Relay 49 | KPR11A (Potter-Brumfield) |
| Transistor 45 | 2N3569 (Fairchild) |
| Transistor 47 | 2N6073 (Motorola) |
| Ammeter 17 | Model 1327 (Simpson) |
| Recorder 18 | Model A601R (Esterline Angus) |
| Rectifiers 13 and 14 | VC-80 (Varo) |
| Rectifier 21 | 1N4006 (TI) |
| Rectifiers 30 and 31 | 1N914 (Motorola) |
| Op. Amps. 29 and 34 | 741TC (Fairchild) |
| Op. Amp. 41 | 734DC (Fairchild) |
| Capacitor 22 | 40µf (Sprague) |
| Capacitor 24 | .1µf (Sprague) |
| Capacitor 33 | .2µf (Sprague) |
| Capacitor 40 | 100µf (Sprague) |
| Resistor 23 | 10 ohms (Eagle) |
| Resistors 25, 26-28 | 20 Kohms (IRC) |
| Resistor 32 | 10 Kohms (IRC) |
| Resistor 35 | 300 Kohms (IRC) |
| Resistors 37, 39, and 42 | 100 Kohms (IRC) |
| Resistor 44 | 1 Kohm (IRC) |
| Resistor 46 | 100 ohms (Allen Bradley) |
| Variable Resistors 36, 38 | 100 Kohms (Beckman) |
| Variable Resistor 43 | 10 Kohms (Beckman) |

We claim:

1. A method for selecting a demulsifier for breaking an emulsion into its constituent phases, comprising the steps of:
   (a) immersing at least two electrodes in a sample of the emulsion,
   (b) applying a sufficient AC voltage to said electrodes to cause breakdown of said emulsion,
   (c) recording the rate of change of the current flow between said electrodes as the current decreases to zero,
   (d) adding a demulsifier to a sample of the emulsion and repeating steps (a) through (c),
   (e) repeating step (d) for a plurality of demulsifiers, and
   (f) monitoring the recordings of said current flow to identify the demulsifier which provides for the most rapid rate of change of said current flow under the application of said voltage.

2. The method of claim 1 further including the step of repeating step (d) for at least two differing concentrations for each demulsifier.

3. The method of claim 1 further including the steps of:
(a) immersing a third electrode in said emulsion sample,
(b) applying each positive half cycle of the AC voltage across a first pair of said electrodes,
(c) applying each negative half cycle of the AC voltage across a second pair of said electrodes, and
(d) measuring the rate of change of current flow through the common electrode of each of said first and second pairs of electrodes.

4. The method of claim 1 wherein said emulsion is a water-in-oil emulsion.

5. The method of claim 4 wherein said emulsion is a crude oil.